US00PP18703P2

(12) United States Plant Patent
Bradford

(10) Patent No.: US PP18,703 P2
(45) Date of Patent: Apr. 1, 2008

(54) NECTARINE TREE NAMED 'JULY BRIGHT'

(50) Latin Name: *Prunus persica*
Varietal Denomination: July Bright

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,880

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP7,506 P 4/1991 Bradford et al.
PP7,918 P 7/1992 Bradford et al.
PP9,961 P 7/1997 Bradford et al.

*Primary Examiner*—Kent Bell

(57) ABSTRACT

The present invention relates to a new and distinct variety of nectarine tree, *Prunus persica,* broadly characterized by a large size, vigorous, hardy, self-fertile, productive and regular bearing tree. The fruit matures under the ecological conditions described in late July, with first picking on Jul. 27, 2006. The fruit is uniformly large in size, mildly acidic and sweet in flavor, globose in shape, clingstone in type, firm in texture, yellow with red bleeding in flesh color, and mostly red in skin color.

1 Drawing Sheet

Botanical classification: *Prunus persica.*
Variety denomination: 'July Bright'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'July Bright'. The present variety was hybridized by me in 1996, grown as a seedling on its own root in my greenhouse, and transplanted to a cultivated area of my experimental orchard located near Le Grand, Calif., in Merced County (San Joaquin Valley).

The variety was developed as a first generation cross using 'Ruby Diamond' (U.S. Plant Pat. No. 7,918) yellow flesh nectarine as the selected seed parent and 'Fire Sweet' (U.S. Plant Pat. No. 9,961) yellow flesh nectarine as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Ruby Diamond' (U.S. Plant Pat. No. 7,918) nectarine, by producing nectarines that are nearly globose in shape, very firm in texture, and mostly red in skin color, but is distinguished therefrom by producing fruit that is clingstone instead of freestone in type, that is yellow with more red bleeding in flesh color, and that matures about seventeen days later.

The present variety is similar to its selected pollen parent, 'Fire Sweet' (U.S. Plant Pat. No. 9,961) nectarine, by producing nectarines that are nearly globose in shape, very firm in texture, clingstone in type, and mostly red in skin color, but is distinguished therefrom by producing fruit that is acidic rather than sub-acidic in flavor, that is yellow with more red bleeding in flesh color, and that matures about eight days earlier.

The present variety is most similar to 'Summer Fire' (U.S. Plant Pat. No. 7,506) nectarine, by producing nectarines that are nearly globose in shape, very firm in texture, clingstone in type, and mostly red in skin color, but is distinguished therefrom by being more productive and by producing fruit that is yellow with more red bleeding in flesh color and that matures about six days earlier.

SUMMARY OF VARIETY

In summary, the present variety is characterized by a large size, vigorous, hardy, self-fertile, productive and regular bearing tree. The fruit matures under the ecological conditions described in late July, with first picking on Jul. 27, 2006. The fruit is uniformly large in size, mildly acidic and sweet in flavor, globose in shape, clingstone in type, firm in texture, yellow with red bleeding in flesh color, and mostly red in skin color.

DRAWING

The accompanying photograph consists of four whole fruits positioned to display the characteristics of the skin color and form, one fruit divided transversely to the suture plane to reveal the flesh and stone, a lower inset showing a bud and blossom, and various leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Aug. 3, 2006, on the original tree during its tenth growing season. All major color code designations are by reference to the Inter-Society Color Council, National Bureau of Standards. Common color names are also used occasionally.

Tree

Size: Large, reaching and maintaining a height of 9' [2.74 m.] and a spread of 12' [3.66 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer with no alternate bearing yet observed.

Approximate chilling requirement: 650 hours.

Trunk:

*Size.*—Medium, reaching a maximum diameter of 6" [152 mm.] after the tenth growing season.

*Texture.*—Shaggy.

*Bark color.*—A Grayish olive [110. gy.Ol] and Dark brown [59. d.Br] variegation with Light yellowish brown [76. l.yBr] crevices present.

*Lenticels.*—Approximate Number Per Square Inch: 6. Color: Moderate yellowish brown [77. m.yBr]. Typical Size: 3/16" [4.8 mm.] to 7/16" [11.1 mm.]. Shape: Eye-shaped to elongated.

Branches:

*Size.*—Diameter of limb is 4" [102 mm.] measured 12" above the crotch. 2¾" [70 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 40 on second year wood. Color: Light yellowish brown [76. l.yBr]. Typical size: 1/32" [0.8 mm.] to ⅛" [3.2 mm.] on second year wood. Shape: Elongated.

Leaves:

*Size.*—Medium. Average Length: 5⅝" [143 mm.]. Average width: 1½" [38 mm.].

*Arrangement.*—Alternate.

*Thickness.*—Medium.

*Form.*—Elliptical.

*Apex.*—Acuminate.

*Base.*—Acute, with a base angle of 70 to 80 degrees.

*Surface.*—Smooth.

*Color.*—Dorsal Surface: Moderate olive green [125. m.OlG]. Ventral Surface: Moderate yellowish green [120. m.YG].

*Margin.*—Finely serrate.

*Venation.*—Pinnately net veined.

*Vein color.*—Light greenish yellow [101. l.gY].

*Petiole.*—Average Length: 5/16" [7.9 mm.]. Average Thickness: 1/32" [0.8 mm.]. Color: Deep greenish yellow [100. deep gY].

*Stipules.*—Number: 2 per leaf, up to 6 per growing tip. Average Length: ⅜" [9.5 mm.]. Color: Strong yellow green [117. s.YG] becoming Moderate reddish brown [43. m.rBr] with maturity.

*Glands.*—Number: 2 to 4. Position: Mostly alternate on petiole and base of blade. Size: Medium. Form: Reniform. Color: Brilliant yellow green [116. brill.YG] becoming Deep yellowish brown [75. m.yBr] with age.

*Leaf buds.*—Pointed, medium.

Flower buds:

*Hardiness.*—Hardy, with respect to central California winters.

*Diameter.*—Typically ¼" [6.4 mm.] 1 week before bloom.

*Length.*—Typically ⅜" [9.5 mm.] 1 week before bloom.

*Form.*—Not appressed.

*Surface.*—Pubescent.

*Color.*—Strong red [12. s.R].

Flowers: Perfect, complete, perigynous, usually a single pistil, typically 24 or more stamens, five sepal and petal locations alternately positioned.

*Type.*—Small.

*Average flower diameter.*—15/16" [23.8 mm.].

*Number of petals.*—Five, extra petal fragments common, double blossoms rarely observed.

*Petal shape.*—Oval.

*Petal margin.*—Wavy.

*Average petal diameter.*—7/16" [11.1 mm.].

*Average petal length.*—9/16" [14.3 mm.].

*Petal apex.*—Rounded.

*Petal base.*—Acute.

*Petal color.*—Pale purplish pink [252. p.pPk] toward the apex with Moderate purplish red [258. m.pR] toward the margin.

*Anther color.*—Moderate reddish orange [37. m.rO] over a Brilliant orange yellow [67. brill.OY] center.

*Stigma color.*—Light greenish yellow [101. l.gY].

*Sepal color.*—A Dark purplish red [259. d.pR] and Strong yellow green [117. s.YG] two tone.

*Sepal length.*—¼" [6.4 mm.].

*Sepal width.*—3/16" [4.8 mm.].

*Average pistil length.*—11/16" [17.5 mm.], often protruding out of the bud before onset of bloom.

*Average stamen length.*—7/16" [11.1 mm.].

*Fragrance.*—Moderate.

*Blooming period.*—Medium, with 'Summer Fire' (U.S. Plant Pat. No. 7,506) nectarine.

*Onset of bloom.*—One percent on Mar. 1, 2006.

*Date of full bloom.*—Mar. 11, 2006.

*Duration of bloom.*—One to two weeks, dependent on ambient temperature.

*Number per cluster.*—1 to 3 with single flowers most common.

FRUIT

Maturity when described: Eating ripe, Aug. 3, 2006.

Date of first picking: Jul. 27, 2006.

Date of last picking: Aug. 7, 2006.
Size: Uniform, large.
*Average diameter axially.*—2 15/16" [74.6 mm.].
*Average diameter across suture plane.*—3" [76.2 mm.].
*Average diameter across cheek plane.*—3 1/16" [77.8 mm.].
*Typical weight.*—7.5 ounces [213 grams].
Form: Globose, symmetrical.
*Longitudinal section form.*—Obovate.
*Axial view.*—Round.
Suture: A sharp groove inside the stem cavity, a shallow trough along the side, and a shallow groove toward the apex ending in a small depression just beyond the pistil point.
Ventral surface: Rounded, lipped toward apex.
Lips: Equal.
Cavity: Flaring, rounded to elongated in the suture plane, suture showing on one side, Very yellow [82. v.Y] stem markings typical.
*Depth.*—7/16" [11.1 mm.].
*Breadth.*—1 1/16" [27.0 mm.].
Base: Truncate.
Apex: Rounded, but appears somewhat cordate if viewed parallel to the suture.
Pistil point: Apical, negligible in length, usually depressed within the suture.
Stem: Medium.
*Average length.*—3/8" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—None observed.
*Color.*—Very deep red [14. v.deep R] over a Strong reddish orange [35. s.rO] background with moderate Light yellow [86. l.Y] freckling toward the apex.
Flesh:
*Color.*—Moderate yellow [87. m.Y] with ample Deep red [13. deep R] bleeding toward the skin and near the stone.
*Surface of pit cavity.*—Very deep red [14. v.deep R] broken fibers when twisted from stone.
*Amygdalin.*—Abundant.
*Juice.*—Moderate.
*Texture.*—Firm, crisp, melting.
*Fibers.*—Abundant, fine.
*Ripens.*—Earlier at the apex.
*Flavor.*—Mildly acidic and sweet.
*Aroma.*—Distinct.
*Eating quality.*—Very good.

STONE

Type: Clingstone.
Form: Oval.
Hilum: Narrow.
Base: Straight.
Apex: Acute, with an average tip angle of 65 to 75 degrees and a tip length of 1/8" [3.2 mm.].
Sides: Equal.
Surface: Regularly furrowed toward the apex, and pitted from base to above center.
Ridges: Rounded.
External color: Light yellowish brown [76. l.yBr].
Pit wall color when cracked: Moderate yellowish brown [77. m.yBr].
Cavity surface color: Strong yellowish brown [74. s.yBr].
Average pit wall thickness: 1/4" [6.4 mm.].
Average width: 1 1/16" [27.0 mm.].
Average length: 1 1/2" [38.1 mm.].
Average breadth: 13/16" [20.6 mm.].
Tendency to split: None observed.
Kernel:
*Form.*—Oval.
*Skin color.*—Strong yellow [84. s.Y] when first removed.
*Pellicle color.*—Grayish yellowish brown [80. gy.yBr].
*Vein color.*—Dark orange yellow [72. d.OY].
*Taste.*—Sweet.
*Viable.*—Yes.
*Average width.*—1/2" [12.7 mm.].
*Average length.*—3/4" [19.1 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Summer Fire' (U.S. Plant Pat. No. 7,506) nectarine, by producing nectarines that are nearly globose in shape, very firm in texture, clingstone in type, and mostly red in skin color, but is distinguished therefrom by being more productive and by producing fruit that is yellow with much more red bleeding in flesh color and that matures about six days earlier.

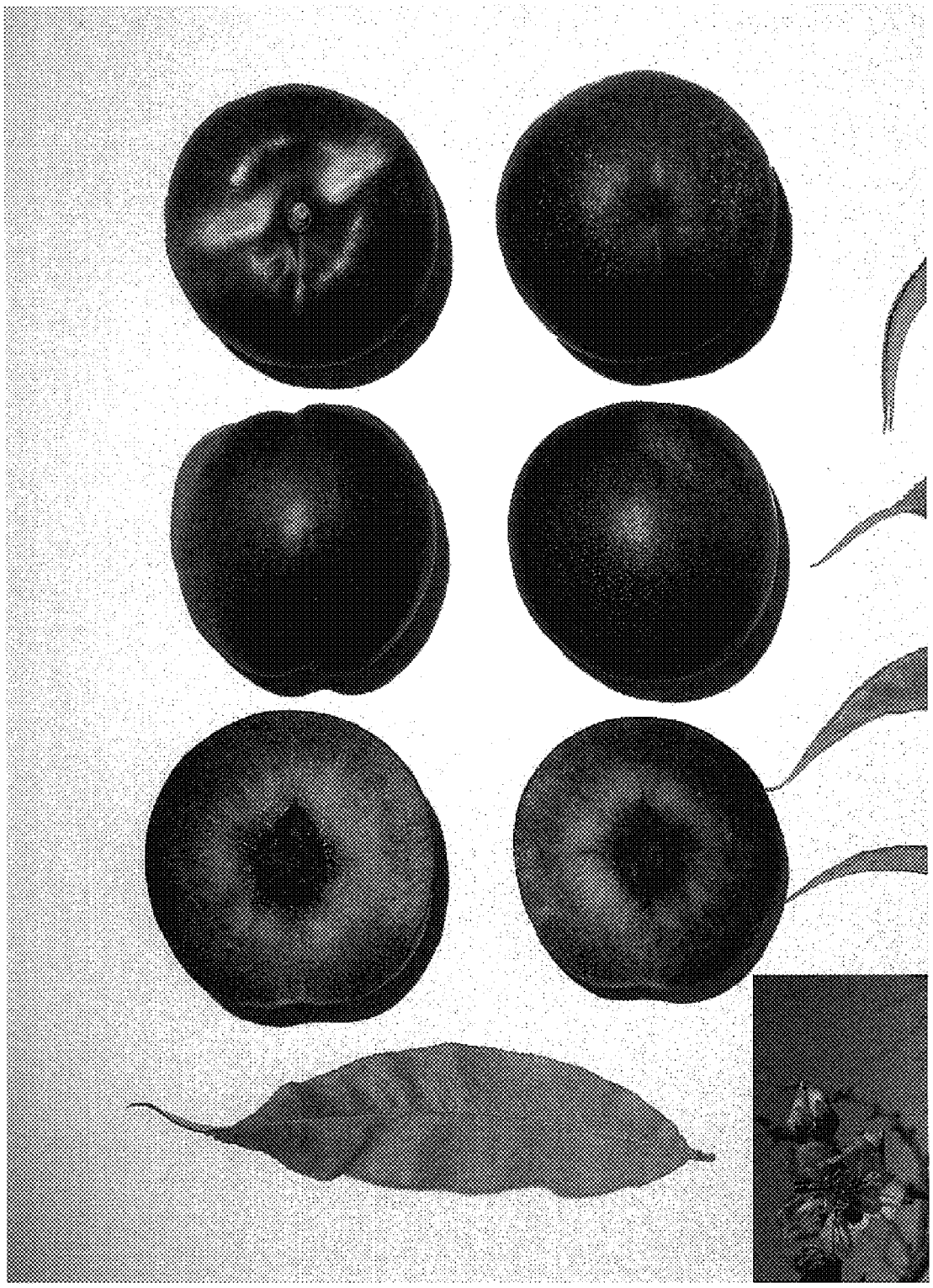

* * * * *